United States Patent
Miranda Olvera et al.

(10) Patent No.: US 10,000,457 B2
(45) Date of Patent: Jun. 19, 2018

(54) PROCESS FOR PREPARING IMIDAZOLIUM BASED IONIC LIQUIDS WITH DI-POLYMERIZED OXIRANE BASE

(71) Applicant: INSTITUTO MEXICANO DEL PETRÓLEO, Mexico City (MX)

(72) Inventors: Alma Delia Miranda Olvera, México (MX); José Manuel Domínguez Esquivel, México (MX); Miguel Ángel Vázquez Guevara, México (MX); Fabiola Irene López Vallejo, México (MX)

(73) Assignee: Instituto Mexicano del Petróleo, Mexico City (MX)

( * ) Notice: Subject to any disclaimer, the term of this patent is extended or adjusted under 35 U.S.C. 154(b) by 0 days. days.

(21) Appl. No.: 15/273,582

(22) Filed: Sep. 22, 2016

(65) Prior Publication Data

US 2017/0088522 A1    Mar. 30, 2017

(30) Foreign Application Priority Data

Sep. 24, 2015    (MX) .................... MX/a/2015/013604

(51) Int. Cl.
  *C07D 233/60*  (2006.01)
  *C08G 65/26*   (2006.01)
  *C07C 51/41*   (2006.01)

(52) U.S. Cl.
  CPC ............ *C07D 233/60* (2013.01); *C07C 51/41* (2013.01); *C08G 65/2618* (2013.01)

(58) Field of Classification Search
  CPC .......................... C07D 233/60; C08G 65/2618
  See application file for complete search history.

(56) References Cited

U.S. PATENT DOCUMENTS 5,077,414 A * 12/1991 Arduengo, III ...... C07D 231/12
                                                   548/335.1

OTHER PUBLICATIONS

Zimmerman, J. et al., "Efficient Synthesis of 1,3-Dialkylimidazolium-Based Ionic Liquids: The Modified Continuous Radziszewski Reaction in a Microreactor Setup", Organic Process Research & Development, 2010, vol. 14, pp. 1102-1109.
Zhang, Q., Zhang, S., Deng, Y., "Recent advances in ionic liquid catalysis", Green Chem., 2011, vol. 13, pp. 2619-2637.
Larsen, A S .; Holbrey, J. D .; Tham, F. S. Redd, "Designing Ionic Liquids: Imidazolium Melts with Inert Carborane Anions", C.A. J. Am. Chem. Soc, 2000, vol. 122(30), pp. 7264-7272.
Seddon, K. R .; "Ionic Liquids for Clean Technology", J. Chem. Tecnol, Biotechnol. 1997, vol. 68, pp. 351-356.
Holbrey, J. D .; Seddon, K. R. J., "The phase behaviour of 1-alkyl-3-methylimidazolium tetrafluoroborates; ionic liquids and ionic liquid crystals", Chem. Soc; Dalton Trans., 1999, pp. 2133-2140.
De Souza, R. F .; Rech, V .; Dupont, J. Adv. Synth. Catal. 2002, vol. 344, 153-155.
Bonhote, P. et al., "Hydrophobic, Highly Conductive Ambient-Temperature Molten Salts", Inor Chem., 1996, vol. 35, 1168-1178.
Dzyuba, S. V. Chem. Commun. 2001, pp. 1466-1467.
Tome, L I. N. et al., "Measurements and Correlation of High-Pressure Densities of Imidazolium-Based Ionic Liquids", LJ Chem. Eng. Data 2008, vol. 53(8), 1914-1921.

(Continued)

*Primary Examiner* — Joseph R Kosack
(74) *Attorney, Agent, or Firm* — Anne M. Reynolds; Casimir Jones, S.C.

(57) ABSTRACT

The present invention relates to a process of synthesis of certain ionic liquids di-polymerized based Radziszewsky type reaction, whereby primary amines containing at least one terminal functional group, for example —OH, aldehydes and a mineral or organic acid, react exothermically in a single step, thus resulting in an ionic liquid by condensation, then oxirane derivative molar quantities are added, by controlling the temperature and pressure a di-polymerized ionic liquid is obtained. The process of the present invention is advantageous because it provides a synthesis scheme for di-polymerized ionic liquids, primarily using short reaction times and high performance; this process can be further scaled for industrial production and it can accept alternative chemical precursors of lower cost.
An example of the general synthesis scheme of ionic liquids-propoxylated di (LI's) imidazolium follows:

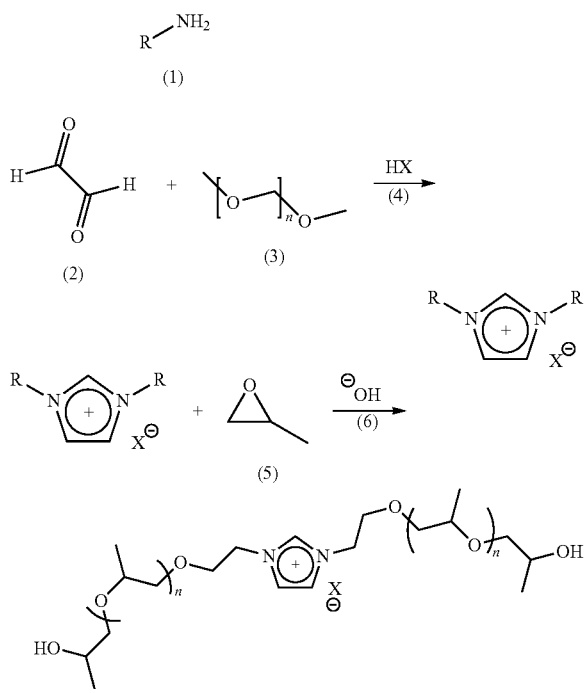

Whereby an efficiency greater than 96% of propoxylated ionic liquid is obtained, the product characterized by spectroscopic data.

13 Claims, No Drawings

(56) References Cited

OTHER PUBLICATIONS

U. Domanska et al., "Solubility of 1-Alkyl-3-ethylimidazolium-Based Ionic Liquids in Water and 1-Octanol", J Chem. Eng. Data, 2008, vol. 53(5), 1126-1132.
Kuhlmann, E. E et al., "Imidazolium dialkylphosphates—a class of versatile, halogen-free and hydrolytically stable ionic liquids", Green Chem. 2007, vol. 9, 233-242.
Blaschette, A et al. Anorg. Allg. Chem. 1983, 506, pp. 75-86.
Wang Z., "Menschutkin Reaction", Z. N. Phys. Chem. 1890, 5, 589, pp. 1897-1900.
Huddleston, J. G. et al., "Characterization and comparison of hydrophilic and hydrophobic room temperature ionic liquids incorporating the imidazolium cation", Green Chem. 2001, vol. 3, 156-164.
Lee, S., "Functionalized imidazolium salts for task-specific ionic liquids and their applications", Chem. Commun., 2006, pp. 1049-1063.
Pucheault, M., Vaultier, M., "Task Specific Ionic Liquids and Task Specific Onium Salts", Top. Curr. Chem., 2009, vol. 290, pp. 83-126.
Giemoth, R. "Task-specific ionic liquids", Angew Chem. Int. Ed., 2010, vol. 49(16), pp. 2834-2839.
Toy, P. H., Janda, K. D., "Soluble Polymer-Supported Organic Synthesis", Acc. Chem. Res., 2000, vol. 33(8), pp. 546-554.
Dickerson, T.D. Reed, N.N., Janda, K. D. Chem. Rev. 2002, 102, 3325-3344.
Benaglia, M., Puglisi, A, Cozzi, F., "Polymer-Supported Organic Catalysts", Chem. Rev., 2003, vol. 103(9), pp. 3401-3429.
Bergbreiter, D. E., Tian, J. H., Hongfa, "Using Soluble Polymer Supports to Facilitate Homogeneous Catalysis", C. Chem. Rev., 2009, vol. 109(2), pp. 530-582.
Lu, J. N., Toy, T. H., "Organic Polymer Supports for Synthesis and for Reagent and Catalyst Immobilization", Chem. Rev., 2009, vol. 109(2), pp. 815-838.
Wang, Y., Luo, J., Liu, Z. J., "Synthesis of a novel 8-hydroxyquinoline functionalized poly (ethylene glycol) bridged dicationic ionic liquid and its application in palladiumcatalyzed Heck reaction under solvent-free conditions", Organomet. Chem., 2013, vol. 739, pp. 1-5.
Ganapatibhotla, L. V. N. R., Zheng, J., Roy, D., Krishnan, S. Chem. Mater., 2010, vol. 22 (23), pp. 6347-6360.
Jadhav V. H. et al., "Tailor-Made Hexaethylene Glycolic Ionic Liquids as Organic Catalysts for Specific Chemical Reactions", Organic Letters, 2011 vol. 13, No. 9, pp. 2502-2505.

* cited by examiner

PROCESS FOR PREPARING IMIDAZOLIUM BASED IONIC LIQUIDS WITH DI-POLYMERIZED OXIRANE BASE

CROSS-REFERENCE TO RELATED APPLICATION(S)

This claims priority to Mexican Patent Application No. MX/a/2015/013604, filed on Sep. 24, 2015, the entire contents of which are fully incorporated herein by reference.

TECHNICAL FIELD OF THE INVENTION

The main object of the present invention is providing a process for preparing di-polymerized compounds to produce ionic liquids with oxirane type derivatives with a variable degree of polymerization, by means of polymerization of oxirane and derivatives of ionic liquids such as di-ethanolamine imidazolium, which have different counter ion.

The present invention provides a process of preparation of salts of dipolymerized 1,3-imidazole, that may involve the reactions of di-polymerized 1,3-imidazole type salts and di-alkanolamine imidazolium salts with oxirane type derivatives.

BACKGROUND OF THE INVENTION

Ionic liquids (ILs) are organic salts with a low melting point and very diverse molecular composition and structure as well as potential applications in several fields. Their structure is consistently ionic and it involves an organic cation and a counter ion that may be organic or inorganic. Initially, these compounds were considered as "green solvents", due to their especial physicochemical properties, for example low vapor pressure, structural stability, etc. The ILs spurred expectations of great interest and have generated more than 6,000 scientific articles published in the last 10 years. Since then, the topic evolved to more sophisticated expectations in the chemical industry and materials engineering applications, such as in the field of catalysis, organometallic chemistry, C—C coupling, etc. Imidazolium like derivatives having distinct alkyl chains attached to the ring-nitrogen atoms are being studied profusely in both symmetric and non-symmetric structures. In addition, the positive charge associated to the organic nucleus imposes its association with a counter ion, which gives a different character as well as several physicochemical properties. Among the most common ILs are the alkyl-trifluoromethanesulfonate amide, bis(trifluoromethylsulfonyl) dicyanamide, hexafluorophosphates, tetrafluoroborates, acetates hydroxides and halides.

The most common method for the synthesis of these ionic liquids is the direct combination of the halide salt with a metal halide, which is used for the synthesis of ionic liquids such as halogenoaluminate (III) and chlorocuprate (I). The latter is particularly sensitive to oxygen which makes it that its use in organic synthesis is rather limited.

Some reports on the synthesis of ionic liquids exhibit different synthesis routes, especially the modifications based on the Radziszewski type reaction (U.S. Pat. No. 5,077,414 Arduengo et al.), who reported the use of reactive α-dicalbonil type, preferably aldehydes in solution, or paraformaldehyde, s-trioxane and/or polyoxymethylene, a primary amine and an acid (preferably with pKa below 2, for example, hydrochloric, sulfuric, etc.), with yields above 98%, reaction times near 0.5 to 24 h and reaction temperatures ranging from −10° C. to 200° C.; likewise, it has been reported (Organic Process Research & Development 2010, 14, 1102-1109) the synthesis of ionic liquids using n-butyl amine as raw material, glyoxal, formaldehyde and tetrafluoroboronic acid, acetic acid and hydrogen chloride, with reaction times ranging from 2 to 20 h, at 10 to 20° C., with yields of less than 59%.

In general, ILs have a hetero-substitution (i.e., 1-alkyl-3-methylimidazolium, where the alkyl group is regularly a group of low molecular weight).

The influence of this hetero-substitution has been the focus of many studies, which indicate that the cations allow the salts to have a low melting point and low viscosity (2). Furthermore, the salts of the hetero-substitution like 1,3-dialkylimidazolium are not selectively obtained by using two different amines in the modified Radziszewski type reaction, which gives a mixture of compounds (3). In this sense, there are few reports about the physicochemical properties (4) and the potential application of homo-substituted imidazolium type salts.

The literature (4) mentioned that derivatives of N-propylamine have a lower viscosity than derivatives from N-butylamine, regardless of the counter ion chosen. Another interesting fact of these homo-substituted derivatives is their thermal stability, which is independent of the chain size and cation type but it seems to diminish with the anion nucleophilicity, which is presumed to involve a nucleophilic attack on the alkyl substituent, an initiator of decomposition (5).

Recently, the functionalization of ionic liquids (FILs), also called ionic liquids for specific tasks (TSILs "task-specific ionic liquids"), covalently incorporate functionality that gives a different reactivity, i.e., ILs with amines, amides, nitriles, ethers, alcohols, acids, ureas and thioureas, which have been designed and synthesized in this way were applied in catalysis, organic synthesis, gas adsorption, analytical chemistry and preparation of new materials (6).

In addition, polyethylene glycols (PEG) are polymers formed from polymerization of oxirane derivatives. These compounds have received more attention from the environmental point of view because they are inexpensive, non-volatile and easily degradable (7). The high reactivity of the oxirane group basis allows to carry out the preparation of compounds with industrial interest, based on alcohols, amines and carboxylic acids, with potential applications in different areas, i.e., IL's-PEG derivatives have been used as solvents in Heck-type coupling reactions (8), electrolytes for energy conversion and energy storage devices, solar cells and super-capacitors (9).

The current trend in the use of LI's involves raw materials that are known for its synthesis purity, which is a major concern in this field. In addition, a growing number of low melting point ILs have not been applied in its liquid state, thus offering new opportunities and discoveries. There is no doubt about the interest in the search and use of new ILs as green solvents, reagents, catalysts and feedstock for the synthesis of new materials. In parallel, there is a marked trend towards the search of new routes for the synthesis of IL's with the purpose of obtaining technical and economic advantages.

In this context, an object of the present invention is to provide a process for the synthesis of ionic liquids based on the imidazolium ring type, which comprises the reaction of primary amines with aldehydes of different type and a mineral inorganic acid, which is carried out by cyclo-condensation type reactions, this is Radziszewski's method, which involves the reaction with oxirane derivatives of di-polymerized ILs to produce a certain degree of polymerization from 2 to more than 50.

REFERENCES

1. Zhang, Q., Zhang, S., Deng, Y. Green Chem., 2011, 13, 2619-2.
2. a) Larsen, A. S.; Holbrey, J. D.; Tham, F. S. Redd, C. A. J. Am. Chem. Soc, 2000, 122, 7264. b) Seddon, K. R.; J. Chem. Tecnol, Biotechnol. 1997, 68, 351. c) Holbrey, J. D.; Seddon, K. R. J. Chem. Soc; Dalton Trans. 1999, 2133.
3. De Souza, R. F.; Rech, V.; Dupont, J. Adv. Synth. Catal. 2002, 344, 153.
4. A) Bonhote, P. Inor Chem. 1996, 35, 1168. B) Dzyuba, S. V. Chem. Commun. 2001, 1466. C) I took, L J Chem. Eng. Data 2008, 53, 1914. D) Domanska, U J Chem. Eng. Data, 2008, 53, 1126. E) Kuhlmann, E. Green Chem. 2007, 9, 233.
5. a) Blaschette, A. et al. Anorg. Allg. Chem. 1983, 506, 75. B) Menschutkin, Z. N. Phys. Chem. 1890, 5, 589. C) Huddleston, J. G. et al., Green Chem. 2001, 3, 156.
6. a) Lee, S., Chem. Commun. 2006 1049-1063. b) Pucheault, M., Vaultier, M. Top. Curr. Chem. 2009, 290, 83-126. c) Giernoth, R. Angew. Chem. Int. Ed. 2010, 49, 2834-2839.
7. Toy, P. H., Janda, K. D. Acc. Chem. Res. 2000, 33, 546-554. b) Dickerson, T. D., Reed, N. N., Janda, K. D., Chem. Rev. 2002, 102, 3325-3344. c) Benaglia, M., Puglisi, A., Cozzi, F., Chem. Rev. 2003, 103, 3401-3429. d) Bergbreiter, D. E., Tian, J. H., Hongfa, C. Chem. Rev. 2009, 109, 530-582. e) Lu, J. N., Toy, T. H., Chem. Rev. 2009, 109, 815-838.
8. Wang, Y., Luo, J., Liu, Z. J. Organomet. Chem., 2013, 739, 1-5.
9. Ganapatibhotla, L. V. N. R., Zheng, J., Roy, D., Krishnan, S. Chem. Mater., 2010, 22 (23), 6347-6360.

DETAILED DESCRIPTION OF THE INVENTION

An analysis of previous results led us to disclose an original process leading to the synthesis of certain ionic liquids with symmetrical di-polymerized based compounds which uses the Radziszewski type reaction, as follows: primary amines, aldehydes and a mineral or organic acid react exothermically in a single step, thus resulting in ILs by condensation, from which molecular groups of the oxirane type are incorporated. Preferably, the ILs are derived from ethanolamine and the degree of polymerization ranges from 2 to over 50, for di-polymerized ionic liquids.

The general scheme shown above illustrates the synthesis of ILs with di-propoxylated (without limiting the use of oxirane derivatives) imidazolium based ILs.

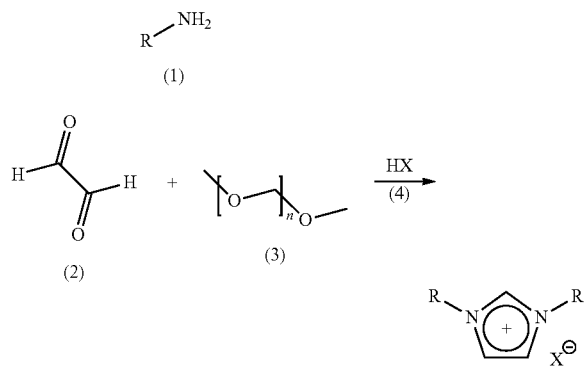

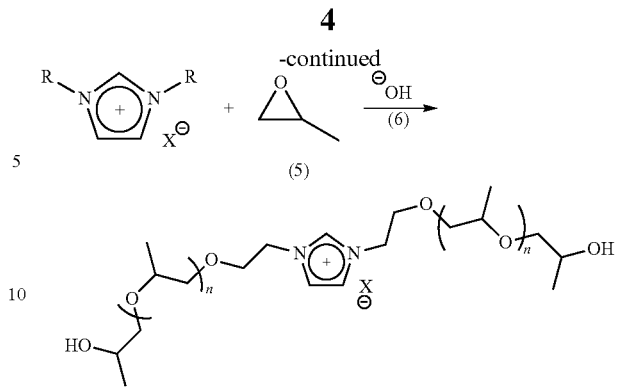

The reaction is performed following this scheme and at least 96% of the product is obtained and further characterized by spectroscopic data, which gives the following:

(1): Primary Amines (R=chains, branches and/or cycles of 2 to 18 carbons) with at least one —OH end group.

(2): Etanedial (oxal-aldehyde)

(3): Poly-oxy-methylene (4): inorganic acid (mineral), preferably hydrochloric acid, sulfuric or nitric, or an organic acid, preferably acetic.

(5): oxiranes, preferably methyloxirane (6): inorganic base, preferably sodium hydroxide, potassium hydroxide or lithium hydroxide.

Thus, the process of the present invention comprises the following steps:

I) Preparation of the reaction mixture. A mono-aldehyde is placed in a reaction system, preferably with poly-oxy-methylene type, together with the reagents that are added preferably in the following sequence: an organic or inorganic acid (mineral) or, similar amino alkanes (2× molar) with at least one terminal —OH group, and a di-aldehyde; in equimolar amounts.

II) Reaction. The reaction mixture obtained in step I is subjected to agitation for 1.5 to 5 h at a temperature ranging between 10 and 40° C., then was left for 1.5 to 3 h, preferably until forming a single phase.

III) The Purification of imidazolium type compounds was performed using a solvent or a mixture of solvents like polar aprotic, or preferably di-chloro-methane, chloroform, ethyl acetate, ethyl ether, etc., more preferably di-chloro-methane; The removal of some reaction products and unreacted materials is obtained by phase transfer at temperatures between 60 and 90° C., under reduced pressure or partial vacuum, for obtaining the pure ionic liquid, for later use.

IV) Characterization of the pure ionic liquid. It is verified that the color and impurities in the pure ILs are eliminated by dissolving it in water, preferably in a volume ratio of IL within 5×, thus passing the solution through a column of active charcoal; the elution agent is frozen and lyophilized to yield pure product, thus giving a yield of at least 98% and, finally, the product is verified by spectroscopic techniques.

V) The ionic liquid obtained in previous stages (1 mol) in a closed stainless steel reactor, with an inorganic base sprayed, is placed in a sealed reactor; thus, the valve connecting the vacuum system opens and the reactor is filled for 30 min, then the vacuum in the reactor has a minimum of −5 psi pressure. The reactor is heated to 120° C. and these conditions are maintained until the moisture content is less than 0.1%; once this value is reached, the reactor contents are heated to 130° C., then at this point the heating is stopped and the addition of oxirane derivative (OD) starts, thus allowing the reactor temperature to increase after the exothermic reaction up to about 170° C.; then, a 90% load OD is added while monitoring the reaction temperature within the range between 140 and 170° C., and a maximum pressure of 58.8 psi (4 kg/cm²), with the control of temperature achieved by a cooling water jacket and by the reactor coil. After addition of 90% oxirane derivative (OD), the supply is stopped and the reaction is left for 30 min. Afterward, the other OD charge is added within a temperature range between 140 and 170° C. At this point a sampling is made along the reaction, as well as the analysis of the cloud point. Once the cloud point is adjusted, the reactor contents are cooled down to about 90° C. and the vacuum system enters to operation for 30 min. Then it follows a cooling down to about 60° C., then the vacuum is broken by allowing air inside and a neutralization with acetic acid is performed, using molar amounts relative to the base.

In this regard, it is important to note that:

The amino-alkanes having a chain from 2 to 18 carbons may be employed in the process described above, these are linear, branched and/or cyclic, but amino-alkanes are preferably linear and branched amino-alkanes with cyclic rings of 3 to 8 carbons, also containing a hydroxy type functional group or any amino-alcohol with a chain of 3 to 18 carbons.

The aldehydes used are preferably:
A di-aldehyde such as Etanedial (oxal-aldehyde), and
A mono-aldehyde as one of poly-oxy-methylene type.

Inorganic or organic acids such as:
Hydrochloric acid in aqueous solution at 30%
Sulfuric acid 98%
Nitric acid 95%
Acetic Acid Polymers are of the oxirane type with functional oxi-type groups, which can be added in a molar ratio from 5 to 50 mol but this not a limiting figure when the pH is less than 10, but no less than 7.5, thus allowing that the reaction elapses at a temperature up to 180° C., but no less than 100° C., in about 1 to 6 h.

The characteristics of the synthesis products were verified by nuclear magnetic resonance (NMR) of $^1H$ and $^{13}C$. For this, a Bruker Avance III machine of 300 MHz was used, with a reference of tetramethylsilane (TMS); the resonance signals of $^1H$ and $^{13}C$ of the solvent were used as internal references; the results are expressed by means of isomer chemical shifts (δ), which are expressed in parts per million (ppm), and are designated as "singlet (s)", "doublet (d)", "triplet (t)", "multiplet (m)"; infrared spectroscopy (IR) was applied too for verifying the products formation, by means of a Perkin-Elmer FTIR-B, model 1600, in the region from 400 to 650 $cm^{-1}$ in series sapphire ATR. Also, the Mass spectra were obtained using a Bruker Instrument Compass 4.0 Data Analysis MicroTOF 10392 II-Q.

EXAMPLES

For a better understanding of the present invention but without limiting its scope, here are presented some practical examples.

Example 1

Synthesis of the Ionic Liquid Chloride N,N-polypropylene-imidazolium

In a flask is added with constant stirring the tri-mer poly-oxy-methylene (1 mol) and hydrochloric acid (1 mol) in aqueous solution at 37%, with stirring for 30 min. at 40° C. Then it was allowed to cool down in ice bath to temperatures below 10° C., then 2-aminoethanol (2 mol) was added drop-wise for about 30 min; once the mixture reach ambient temperature, stirring continues for 30 min, then ethanedial in aqueous solution (40%) is added, leaving for additional 30 min at room temperature. Then, the temperature is increased to 35-40° C. for 5 h. It is placed in the rotating evaporator ("rotavapor") at 70° C. at 50 mbar. Under these conditions the yield is 96%. The product is then characterized by spectroscopic data: IR 3311, 3123, 2910, 1658, 1561, 1159, 1067 $cm^{-1}$; $^1H$ NMR (300 MHz, DMSO-d6) δ (ppm) 3.7-3.3 (m, 4 H), 4.4 (m, 4 H), 7.8 (d, 2H), 9.23 (s, 1H); $^{13}C$ NMR (300 MHz) δ (ppm) 51.66, 58.0, 122.6, 136.6; HRMS calculated 192.6402 $C_7H_{13}ClN_2O_2$, being 192.0775.

The ionic liquid, chloride N,N-diethanol-imidazolium (1 mol) is placed in a Parr reactor, then the valve connecting the vacuum system is open and the reactor is evacuated for 30 min, then the sodium hydroxide is loaded with the same vacuum sealing the reactor, then plugs are placed on the vent valves and sampling at the bottom allows to verify that the vacuum in the reactor is at least −5 psi. The reactor contents are heated to 120° C. for removing moisture down to less than 0.1%, thus the value of moisture is verified and the reactor contents are heated up to 140° C., once this temperature is reached, the heating is suspended and it starts the addition of propylene oxide (PO) (8 mol), thus allowing the reactor temperature to increase by the heat flow that is generated by the reaction exothermicity up to 170° C.; afterwards, there is a 90% loading of PO, always keeping the security issues until the reaction temperature is in the range between 140 and 170° C., and a maximum pressure inside the reactor of 4 $Kg/cm^2$; in this case the temperature is controlled by introducing cooling water into the jacket and in the reactor coil. After addition of 90% charge of propylene oxide (PO), the PO supply is closed and the reaction is allowed for 30 min. Once this step occurs, the other charge of PO is allowed in at a temperature range between 140 and 170° C. After 1 h reaction, there is a take of sample and the cloud point is analyzed. Once this parameter is adjusted, the reactor content is cooled down to 90° C., then it is connected to the vacuum system to make the maximum vacuum for 30 min. Then, the system is cooled down to 60° C. and the vacuum is broken with air, then it is neutralized with acetic acid in molar amounts, relative to the soda. Under these conditions the yield is higher than 99%. The product was characterized by spectroscopic data: IR 3375, 3123, 2967, 2873, 1663, 1579, 1458, 1374, 1104 $cm^{-1}$; $^1H$ NMR (300 MHz, DMSO-d6) δ (ppm) 0.98 to 1059 (m), 2.32-2.40 (m), 3.13-3.75 (m), 7.66 (s), 7.69 (d), 7.95 (s); $^{13}C$ NMR (300 MHz) δ (ppm) 17.23, 20.18, 48.3, 54.5, 65.50, 67.32, 74.46, 76.81,121.6,172.5; Mw=487.215.

Example 2

Synthesis of Acetate Ionic Liquid N,N—N,N-polypropylene-imidazolium

In a flask the tri-mer poly-oxy-methylene (1 mol) is added with constant stirring and glacial acetic acid (1 mol), then it is stirred for 30 min. at 40° C., then it is allowed to cool down within an ice bath, to a temperature below 10° C.; then, 2-aminoethanol (2 mol) is added drop-wise for about 30 min., until the addition is complete after keeping under stirring for 30 minutes at room temperature, then ethanedial in aqueous solution (40%) is added left for additional 30 min., both mixtures at room temperature. When this step is complete, the temperature is increased to 35-40° C. for 5 h.

Under these conditions the yield is 95%. The product was characterized by spectroscopic data: IR 3311, 3123, 2910, 1780, 1658, 1561, 1159, 1067 cm$^{-1}$; $^1$H NMR (300 MHz, DMSO-d6) δ (ppm) 2.2 (s, 3H), 3.7-3.3 (m, 4 H), 4.4 (m, 4 H), 7.8 (d, 2H), 9.23 (s , 1 HOUR); $^{13}$C NMR (300 MHz) δ (ppm) 23.4, 51.66, 58.0, 122.6, 136.6, 177.2; HRMS calculated 216.2392 C$_9$H$_{16}$N$_2$O$_4$, being 216.1175. The ionic liquid, acetate N,N-diethanol-imidazolium (1 mol) in a Parr reactor is placed, then the valve connecting the vacuum system is open and it is evacuated into the reactor, for 30 min., then liquid soda is added by using the same vacuum, thus sealing the reactor and placing caps on the vent valves, sampling is performed and it is verified that the vacuum in the reactor is at least −5 psi. The reactor contents are then heated to 120° C., an empty set, and these conditions are maintained for the time to remove the moisture to less than 0.1%; once the correct value of moisture is reached, the reactor contents are heated up to 130° C. and, upon reaching this temperature, the heating is suspended and the addition of propylene oxide (PO) (8 mol) is started, allowing that the reactor temperature increases by the heat generated by the exothermic reaction up to 150° C., then a 90% load of PO is added, always verifying that the reaction temperature is within a range between 140 and 150° C., and a maximum pressure inside the reactor of 4 kg/cm$^2$; the temperature is controlled by introducing cooling water in the jacket and in the reactor coil. After addition of the 90% charge of propylene oxide (PO), PO supply is closed and the reaction is left for 30 min. Once this step is over, the other charge of PO is added at temperatures between 140 and 150° C. After 1 h reaction, it is sampled and the cloud point is measured. Once the cloud point is verified, the reactor contents are cooled down to 90° C. and the vacuum stage is connected for 30 min. Then the system is cooled down to 60° C. and the vacuum is broken with air and then neutralized with acetic acid in molar amounts, relative to the soda. Under these conditions the yield is higher than 96%. The product was characterized by spectroscopic data: IR 3375, 3123, 2967, 2873, 1780, 1663, 1579, 1458, 1374, 1104 cm$^{-1}$; $^1$H NMR (300 MHz, DMSO-d6) δ (ppm) 0.98 to 1059 (m), 2.2 (s, 3H), 2.32-2.40 (m), 3.13-3.75 (m), 7.66 (s), 7.69 (d), 7.95 (s); 13C NMR (300 MHz) δ (ppm) 17.23, 20.18, 23.4, 48.3, 54.5, 65.50, 67.32, 74.46, 76.81, 121.6, 172.5, 177.2; Mw=546.255.

The invention claimed is:

1. A process for producing an ionic liquid with di-polymerized imidazolium base, the process comprising the steps of:
   I) mixing in a reaction system
      an aldehyde source
      an organic or inorganic acid,
      a primary amine R—NH$_2$, wherein R is a chain of 2 to 18 carbons having at least one —OH terminal group, the chain being linear, branched, or cyclic, and
      oxal-aldehyde to form a reaction mixture,
   II) allowing the reaction mixture to react at a temperature between 10 and 150° C. to produce an imidazolium compound,
   III) isolating the imidazolium compound of step II), and
   IV) reacting the isolated imidazolium compound of step III) with an oxirane derivative in the presence of an inorganic base to produce the ionic liquid with di-polymerized imidazolium base.

2. The process according to claim 1, wherein R is a chain of 3 to 8 carbons.

3. The process according to claim 1, wherein the aldehyde source used in step I) is poly-oxy-methylene.

4. The process according to claim 1, wherein the inorganic acid used in step I) is hydrochloric acid, sulfuric acid, or nitric acid, and wherein the organic acid used in step I) is acetic acid.

5. The process according to claim 1, wherein the oxirane derivative used in step IV) is methyloxirane.

6. The process according to claim 1, wherein at least part of reaction of step IV) is carried out under a pressure of 55-210 psi.

7. The process according to claim 1, wherein at least part of reaction of step IV) is carried out at a temperature of between 140 and 170° C.

8. The process according to claim 1, wherein the molar ratio of the isolated imidazolium compound to the oxirane derivative in step IV) is from 1:1 to 1:50.

9. The process according to claim 1, the inorganic base used in step IV) is sodium hydroxide, potassium hydroxide, or lithium hydroxide.

10. The process according to claim 1, wherein the yield of step IV) is at least 96%.

11. The process according to claim 1, wherein step II) is carried out at a temperature between 10 and 40° C.

12. The process according to claim 1, wherein step II) further comprises
    stirring the reaction mixture for a first period of 1.5 to 8 hours at a temperature between 10 and 150° C. to produce the imidazolium compound, and
    maintaining stirring for a second period to produce a single phase.

13. The process according to claim 12, wherein the first period is 1.5 to 5 hours carried out at a temperature between 10 and 40° C., and the second period is at least 2 hours.

* * * * *